United States Patent [19]

Seneker et al.

[11] Patent Number: 5,233,079
[45] Date of Patent: Aug. 3, 1993

[54] FREE FLOWING SOLIDS BASED ON 4,4'DIISOCYANATO DICYCLOHEXYLMETHANE

[75] Inventors: Stephen D. Seneker, Paden City, W. Va.; Peter H. Markusch, Pittsburgh, Pa.

[73] Assignee: Miles Inc., Pittsburgh, Pa.

[21] Appl. No.: 772,996

[22] Filed: Oct. 8, 1991

[51] Int. Cl.$^5$ .......................................... C07C 263/20
[52] U.S. Cl. .................................. 560/352; 560/330; 560/336
[58] Field of Search ...................... 560/330, 336, 352

[56] References Cited

U.S. PATENT DOCUMENTS

| | | | |
|---|---|---|---|
| 2,606,925 | 8/1952 | Whitman | 564/449 |
| 3,155,724 | 11/1964 | Arthur | 564/444 |
| 3,789,032 | 1/1974 | Hoeschele | 528/63 |

FOREIGN PATENT DOCUMENTS

| | | |
|---|---|---|
| 971184 | 7/1975 | Canada . |
| 443139 | 2/1991 | European Pat. Off. . |
| 1127338 | 9/1968 | United Kingdom . |
| 1220715 | 1/1971 | United Kingdom . |

OTHER PUBLICATIONS

*Derwent Publications Ltd.*, JP-A-53 046 945, (Mitsui Toatsu), Apr. 27, 1978, Abstract only.

*Primary Examiner*—José G. Dees
*Assistant Examiner*—Vera C. Clarke
*Attorney, Agent, or Firm*—Joseph C. Gil; Godfried R. Akorli

[57] ABSTRACT

Disclosed herein is a free-flowing solid of 4,4'-diisocyanato dicyclohexylmethane consisting essentially of at least 90 percent of the trans,trans isomer.

4 Claims, No Drawings

FREE FLOWING SOLIDS BASED ON 4,4'DIISOCYANATO DICYCLOHEXYLMETHANE

BACKGROUND OF THE INVENTION

The present invention relates to polyisocyanates containing 4,4'-diisocyanato dicyclohexylmethane having a high content of the trans,trans isomer. More specifically, the present invention relates to a free flowing solid polyisocyanate based on 4,4'-diisocyanato dicyclohexylmethane.

4,4'-diisocyanato dicyclohexylmethane (alternately referred to as "PICM") is a cycloaliphatic diisocyanate of low volatility. PICM and other aliphatic isocyanates are useful in the preparation of non-discoloring polyurethanes. In general, such isocyanates are reacted with glycols and/or polyols and chain extenders and/or cross linkers. Such isocyanates are particularly useful in the preparation of polyurethane coatings and elastomers. PICM and the diamine precursor, 4,4'-diamino dicyclohexylmethane ("PACM"), exist, in three stereoisomeric forms (i.e., trans,trans; cis,trans; and cis,cis) as described, for example, in U.S. Pat. Nos. 2,606,925, and 3,789,032, Canadian Patents 961,049 and 971,184, and British Patent 1,220,715. Commercial grades of PACM and PICM normally contain all three isomers.

The most direct method of producing PICM is to first hydrogenate diamino diphenylmethane to form a mixture of the stereoisomers of PACM, and to then phosgenate the mixture. When the synthesis of PICM is conducted using readily available mixtures of stereoisomers of PACM (such as the equilibrium mixture described in U.S. Pat. No. 3,155,724), the PICM obtained is a slush or slurry at normal operating temperatures, having a melting point of about 58° C., which corresponds to a trans,trans-isomer content of about 54%. Various art-known PICM mixtures have trans,trans-isomer contents of from about 17 to about 55% by weight. In addition, the art has recognized an advantage in utilizing high trans,trans-isomer PICM in producing elastomers (see, U.S. Pat. No. 3,789,032).

In order to prepare PICM of relatively high trans, trans-isomer content, the art has generally used a PACM having a relatively high trans,trans-isomer content in the phosgenation reaction. Various methods are known for treating PACM to obtain the requisite high trans,trans-isomer content. Crystallization techniques have been described in the art. See, e.g., U.S. Pat. Nos. 2,494,563, 3,153,088, 3,384,661 and 3,393,236. The crystallization of PACM suffers from various disadvantages. PACM readily forms a precipitant when exposed to carbon dioxide, causing problems in filtering and contamination of the crystals (see, U.S. Pat. No. 2,494,563, column 3, lines 26-29, and column 4, lines 72-75). In addition, PACM is generally difficult to crystallize since it will easily form a supercooled liquid. The prior art has overcome this problem by adding seed crystals (U.S. Pat. No. 2,494,563), by lowering the viscosity by using an inert solvent (U.S. Pat. Nos. 2,494,563, 3,153,088, 3,393,236 and 3,384,661), or by forming an adduct of PACM that crystallizes better, such as the hydrate (U.S. Pat. No. 3,153,088) or the alcoholate (U.S. Pat. No. 3,384,661). Such an adduct must be treated to remove water or alcohol before phosgenating to PICM.

U.S. Pat. No. 4,983,763 describes a process for preparing PICM of relatively high trans,trans isomer content; said process comprises crystallization of PICM. However, it does not teach that PICM can be obtained in the form of a free-flowing solid.

Generally put, it seems that although processes for preparing PICM of high trans,trans contents are known in the art, the nature of PICM as free-flowing solids, in commercially useful quantities, has not been realized. To date, the art known commercially available PICMs are obtained in the form of solutions and slurries. The present invention provides in commercial quantities a free-flowing solid based on 4,4'-diisocyanato dicyclohexylmethane.

SUMMARY OF THE INVENTION

In accordance with the foregoing, the present invention encompasses a free-flowing solid of 4,4'-diisocyanato dicyclohexylmethane consisting essentially of at least 90 percent and preferably from about 95 to 99 percent of its trans-trans isomer.

As would be realized, in the form of free-flowing solids, the diisocyanates of this invention can be more tractable. Compared to art-related compositions which are fused solids or slurries at ambient temperature, the free-flowing solids are easier and less expensive to transport. Compared to art related compositions which are fused solids or slurries, the free flowing solids have a homogeneous composition without the need to melt them at elevated temperature. With low vapor pressure, the free flowing solids can be weighed and safely combined with suitable coreactants, at ambient temperatures.

The free flowing solid isocyanates can be reacted with active hydrogen containing materials to produce polyurethane and/or polyurea reaction products with the desirable properties. These and other aspects of the invention are described more fully below.

DETAILED DESCRIPTION OF THE INVENTION

The free-flowing solids of the claimed invention can be characterized as particulate materials which have less than 50 percent by weight of the solid particles as agglomerates. In the preferred embodiment of the invention, no less than 50% by weight of the solids is in a free-flowing form, at ambient temperatures ranging from room temperature to about 50 degrees Centigrade. In the particularly preferred embodiment of the invention, no less than 80 percent by weight of the particles agglomerate.

The free flowing solids of the invention can be prepared by a relatively simple process comprising employing a PICM containing a relatively high amount of the trans,trans-isomer. More particularly, the present invention is directed to a process for the preparation of free flowing solids of a 4,4'-diisocyanato dicyclohexylmethane containing at least 90% by weight, and preferably at least 95-99% by weight, of the trans,trans isomer comprising:

(a) melting a mixture of 4,4'-diisocyanato dicyclohexylmethane isomers containing at least 30% by weight, and preferably from 45 to 55% by weight, of the trans,trans isomer, (b) cooling the melted mixture to a temperature of from about 20° to about 25° C. to form:

(1) a liquid phase which contains from about 18 to about 25% by weight of the trans,trans isomer, and (2) a solid phase which contains from about 70 to about 85% by weight of the trans,trans isomer, (c) removing said liquid phase (which is a commercially viable product), (d) dissolving said solid phase in a solvent to form a 4,4'-diisocyanato dicyclohexylmethane-containing solution, (e) allowing said solution to remain at room temperature for a time sufficient to form:

(1) a solid phase containing at least 90% by weight, and preferably at least 98% by weight of the trans,trans isomer, and (2) a liquid phase containing said solvent and a mixture of 4,4'-diisocyanato dicyclohexylmethane isomers containing from 30 to 70% by weight, and preferably from 45 to 55% by weight of the trans,trans isomer, (f) removing said liquid phase (e)(2), (g) removing the solvent from said solid phase (e)(1), and (h) removing said solid phase by melting (e)(1), followed by (i) converting the resultant melt by cooling it to a free flowing form.

In the most preferred embodiment, the solvent is removed from the liquid phase (e)(2) and returned to step (d), and the residue remaining after the solvent removal is returned to step (a).

In accordance with the invention, the solid phase removed per step (h) is substantially pure in that it is free of or substantially free of impurities such as residual solvents. Without being bound to any particular theory, it is believed that the presence of the impurities or by-products at the surface of the new solid particles would vitiate the free flowing nature of the solids. Hence the removal of solvent from the solids must be effective to produce the free-flowing solids of the invention.

Substantially any mixture of PICM containing at least 30% by weight, and preferably containing from 45 to 55% by weight, of the trans,trans isomer can be used in step (a) of the process of the invention. It is generally preferable to utilize mixtures which typically contain about 50% by weight of the trans,trans isomer. The particular mixture selected is melted, typically by heating to a temperature of from 60° to 90° C. for a period of from 60 to 120 minutes. The melted mixture is then cooled to a temperature of from about 20° to about 25° C. to form liquid and solid phases having the trans,trans isomer contents noted above. Typically, the melt is cooled to the requisite temperature in from 180 to 360 minutes, and is held at that temperature for from 120 to 360 minutes.

The liquid and solid phases formed by cooling the melt can be separated by substantially any technique known in the art, such as, for example, filtration, decanting, centrifuging or the like. Once the two phases are separated, the solid phase is then dissolved in an appropriate solvent. Useful solvents include hydrocarbons such as cyclohexane, heptane and hexane; aromatic solvents such as toluene; ketones such as methylethyl ketone, methylisobutyl ketone and acetone; esters such as ethyl acetate and butyl acetate; ethers such as diethyl ether; and chlorine containing solvents such as monochlorobenzene. Cyclohexane is the presently preferred solvent. In general, the amount of solvent used ranges from 10 to 30% by weight based on the total weight of the PICM and the solvent. Of course, higher amounts of solvent could be used, but the overall yield would be reduced.

Once the PICM is dissolved in the solvent, the resultant solution is allowed to remain at room temperature (typically from 20° to 25° C.) for a time sufficient to form two phases having the trans,trans isomer content noted under step (e) above. In general, a time of from 60 to 360 minutes at room temperature is sufficient to allow formation of the two phases. The two phases can then be separated by substantially any technique known in the art which would ensure that the solid thus obtained is free of impurities such as residual solvent.

On the industrial scale, it is preferred to separate the solid and liquid phases by simply draining the liquid phase from the crystallizer. The solid phase is then melted at about 90° C. and the residual solvent removed by distillation. The melted PICM having a trans,trans content of at least 90 weight percent and free of residual solvent is then converted into a free flowing solid by cooling and optionally granulating the resultant melt. This can be done, for example, by casting the melted PICM on a cooled belt under an inert atmosphere and converting it into a free flowing solid using a granulator and or any kind of grinder if a smaller particle size is desired. Effective cooling is conducted per a time/temperature schedule at which there can be obtained a solid having substantially the same isomeric composition as the melt. Typically, a period of 1 second to 60 seconds, at a temperature of −60° C. to 25° C. is sufficient to provide effective cooling. The free flowing solid can be in various forms such as flakes, granules, or powder.

The advantage in the preparation of isocyanate reaction products lies in the fact that a pre-measured (weighted) amount of the free-flowing solids can be added to the suitable coreactants at ambient temperature and the product cured without prior conversion into a liquid form as would be necessary for fused solids or slush materials. Liquification of PICM that contains high concentrations of the trans,trans isomer usually requires temperatures above 80° C. which causes handling problems. Hot liquid isocyanates can cause severe injuries when they come in contact with the skin or eyes; due to the higher vapor pressure at elevated temperature they can enter the respiratory system. By this invention, these problems can be avoided.

In the practice of the invention, an isocyanate reaction product can be prepared by reacting the free-flowing solid of claimed invention with an active hydrogen group containing material. The active hydrogen group can be a hydroxyl, amine group or a combination thereof. Specific but non-limiting examples of the active hydrogen containing materials can polyols, polyamine, or hydroxyl-functional amines wherein the active hydrogen group is a hydroxyl group and/or amino group. The resultant isocyanate reaction product can be a polyurethane, polyurea or polyurethane-urea or the like.

The invention is further illustrated but is not intended to be limited by the following examples in which all parts and percentages are by weight unless otherwise specified.

EXAMPLES

Preparation of the Starting Materials

About one-gallon of 4,4'-diisocyanato dicyclohexylmethane containing 50.1% by weight of the trans,-trans isomer (PICM-50.1) in a glass jar was completely melted at 90° C. The melt was allowed to crystallize by cooling to ambient temperature and held at that temperature for 16 hours. The liquid and solid phases were then separated by simply inverting the glass jar and draining the liquid phase. The solid phase contained 79.9% by weight of the trans,trans isomer (PICM-79.9).

To 80 parts of the 79.9% trans,trans-4,4'-diisocyanato dicyclohexylmethane were added 20 parts of the cyclohexane solvent. The mixture was heated to 70° C. to solubilize the PICM-79.9 and cyclohexane. The solution was then allowed to cool to ambient temperature and crystallize at that temperature for at least 24 hours. The solids were vacuum filtered to remove the liquid phase and the residual cyclohexane removed by heating in a vacuum (1 mm Hg) for 8 hours at 60° C. The solid phase contained 99.1% by weight of the trans,trans isomer. The PICM-79.9 and PICM-99.1 were used to prepare the materials in Examples 2, 3 and 4.

EXAMPLE 1

A 200 gram sample of 4,4'-diisocyanato dicyclohexylmethane containing 98.4% of the trans,trans isomer was ground in a ceramic ball mill for 24 hours. After grinding the PICM-98.4 to a powder, it was sieved to obtain a sample with a particle size distribution between 250 and 420 microns. Portions of this sample (8.3 grams) were added to two small glass bottles. One of the glass bottles was left undisturbed at ambient temperature and the other in a 50 degrees Centigrade oven. After three weeks, the samples were sieved again to determine if the particles had agglomerated. About 98 percent of the sample held at ambient temperature passed through a 420 micron sieve. About 95 percent of the sample held at 50 degrees Centigrade passed through the 420 micron sieve.

EXAMPLE 2

A 4,4'-diisocyanato dicyclohexylmethane containing 95 percent of the trans,trans isomer was prepared by blending 158 grams of PICM-99.1 and 42 grams of PICM-79.9 mixture was melted at 90° C. until homogeneous and then solidified by pouring about 25 grams each into one quart metal cans, sealing the cans, and then immersing them in a dry ice/acetone bath for 45 minutes. The resulting white solid was transferred to a ceramic ball mill and ground for 24 hours.

After grinding the PICM-95 to a powder, it was sieved to obtain a sample with a particle size distribution between 250 and 420 microns. Portions of this sample (6.8 grams) were added to two small glass bottles. One of the glass bottles was left undisturbed at ambient temperature and the other in a 50° C. oven. After three weeks, the samples were sieved again to determine if the particles had agglomerated. About 95% of the sample held at ambient temperature passed through a 420 micron sieve. About 81 percent of the sample held at 50° C. passed through the 420 micron sieve.

EXAMPLE 3

A 4,4'-diisocyanato dicyclohexylmethane containing 90 percent of the trans,trans isomer was prepared by blending 106 grams of PICM 99.1 and 94 grams of PICM-79.9. The mixture was melted at 90° C. until homogeneous and then solidified by pouring about 25 grams each into one quart metal cans, sealing the cans, and then immersing them in a dry ice/acetone bath for 5 minutes. The resulting white solid was transferred to a ceramic ball mill and ground for 24 hours.

After grinding the PICM-90 to a powder, it was sieved to obtain a sample with a particle size distribution between 250 and 420 microns. Portions of this sample (6.6 grams) were added to two small glass bottles. One of the glass bottles was left undisturbed at ambient temperature and the other in a 50° C. oven. After three weeks, the samples were sieved again to determine if the particles had agglomerated. About 64% of the sample held at ambient temperature passed through a 420 micron sieve. About 52% of the sample held at 50° C. passed through the 420 micron sieve.

EXAMPLE 4 (Comparative)

A 4,4'-diisocyanato dicyclohexylmethane containing 85 percent of the trans,trans isomer was prepared by blending 54 grams of PICM-99.1 and 146 grams of PICM-79.9. The mixture was melted at 90° C. until homogeneous and then solidified by pouring about 25 grams each into one quart metal cans, sealing the cans, and then immersing them in a dry ice/acetone bath for 5 minutes. The resulting white solid was transferred to a ceramic ball mill and ground for 24 hours.

After grinding the PICM-85 to a powder, it was sieved to obtain a sample with a particle size distribution between 250 and 420 microns. Portions of this sample (5.5 grams) were added to two small glass bottles. One was left undisturbed at ambient temperature and the other in a 50° C. oven. After three weeks, the samples were sieved again to determine if the particles had agglomerated together. Only 2 percent of the sample held at ambient temperature passed through a 420 micron sieve. Only 3 percent of the sample held at 50° C. passed through the 420 micron sieve.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A free-flowing solid of 4,4'-diisocyanato dicyclohexylmethane consisting essentially of at least 90 percent of the trans,trans isomer.

2. The free-flowing solid of claim 1 wherein the trans,trans isomer is present in an amount of about 95 to 99 percent.

3. The free-flowing solid of claim 1 wherein not more than 50 percent by weight of the solid particles is agglomerated at temperatures ranging from room temperature to 50° C.

4. A process for the preparation of free flowing solids of a 4,4'-diisocyanato dicyclohexylmethane comprising:
   (a) melting a mixture of 4,4'-diisocyanato dicyclohexylmethane isomers containing at least 30 to 55% by weight, of the trans,trans isomer,
   (b) cooling the melted mixture to a temperature of from about 20° to about 25° C. to form:
      (1) a liquid phase which contains from about 18 to about 25% by weight of the trans,trans isomer, and
      (2) a solid phase which contains from about 70 to about 85% by weight of the trans,trans isomer,
   (c) removing said liquid phase,
   (d) dissolving said solid phase in a solvent to form a 4,4'-diisocyanato dicyclohexylmethane-containing solution,
   (e) allowing said solution to remain at room temperature for a time sufficient to form:

(1) a solid phase containing at least 90% by weight, of the trans,trans isomer, and
(2) a liquid phase containing said solvent and a mixture of 4,4'-diisocyanato dicyclohexylmethane isomers containing from 30 to 70% by weight of the trans,trans isomer,
(f) removing said liquid phase (e)(2),
(g) removing the residual solvent from said solid phase (e)(1), and
(h) removing said solid phase by melting (e)(1), followed by
(i) converting the resultant melt by cooling it to a free flowing form.

* * * * *